United States Patent
Carpentier et al.

(10) Patent No.: US 6,210,957 B1
(45) Date of Patent: Apr. 3, 2001

(54) APPARATUSES FOR TREATING BIOLOGICAL TISSUE TO MITIGATE CALCIFICATION

(75) Inventors: Sophie Carpentier; Alain F. Carpentier, both of Paris (FR); Lillian J. Quintero, Garden Grove, CA (US); Victor S. Packham, Costa Mesa, CA (US); Jong H. Wang, Rancho Palos Verdes, CA (US); Stefan G. Schreck, Vista, CA (US)

(73) Assignee: Edwards Lifescience Corporation, Irvine, CA (US)

( * ) Notice: Subject to any disclaimer, the term of this patent is extended or adjusted under 35 U.S.C. 154(b) by 0 days.

(21) Appl. No.: 09/283,596

(22) Filed: Apr. 10, 1999

Related U.S. Application Data

(62) Division of application No. 08/874,180, filed on Jun. 13, 1997, now Pat. No. 5,931,969, which is a continuation of application No. 08/282,358, filed on Jul. 29, 1994, now abandoned.

(51) Int. Cl.[7] .................................................. A01N 1/00
(52) U.S. Cl. ...................................... 435/284.1; 435/307.1
(58) Field of Search ............................. 435/284.1, 289.1, 435/297.1, 297.2, 297.5, 303.1, 307.1

(56) References Cited

U.S. PATENT DOCUMENTS

| | | |
|---|---|---|
| 2,393,580 | 1/1946 | Weiskopf . |
| 3,002,895 | * 10/1961 | Freedman . |
| 3,093,439 | 6/1963 | Bothwell . |
| 3,870,789 | 3/1975 | Mikat ........................................ 424/3 |
| 3,927,422 | 12/1975 | Sawyer ........................................ 3/1 |
| 3,961,097 | 6/1976 | Gravlee, Jr. ............................... 427/2 |
| 3,966,401 | 6/1976 | Hancock et al. ...................... 8/94.11 |
| 4,050,893 | 9/1977 | Hancock et al. ...................... 8/94.11 |
| 4,082,507 | 4/1978 | Sawyer et al. ........................ 8/94.11 |
| 4,120,649 | 10/1978 | Schecter ................................ 8/94.11 |
| 4,323,358 | 4/1982 | Lentz et al. ........................... 8/94.11 |
| 4,350,492 | 9/1982 | Wright et al. ......................... 8/94.11 |

(List continued on next page.)

FOREIGN PATENT DOCUMENTS

| | | |
|---|---|---|
| WO 95/34332 | 12/1993 | (WO) . |
| WO 95/11047 | 4/1995 | (WO) . |
| WO 95/22361 | 8/1995 | (WO) . |
| WO 96/04028 | 2/1996 | (WO) . |
| WO 96/13227 | 5/1996 | (WO) . |

OTHER PUBLICATIONS

Allied Fischer Scientific Product Catalogue, pp. 914, 1986.*
Sealed Information Submission Under MPEP § 724.

*Primary Examiner*—David A. Redding
(74) *Attorney, Agent, or Firm*—Gay L. Cumberbatch

(57) ABSTRACT

An apparatus for treating fixed biological tissue to inhibit calcification of the biological tissue following implantation thereof in a mammalian body. The apparatus includes a container for placing the biological tissue in contact with a treatment solution, structure to induce relative tissue/solution movement, and structure to heat the solution. The relative movement may be induced by shaking a container in which the tissue is immersed in the treatment solution, or by stirring the solution within the container. The movement may also be induced by flowing a treatment solution past the tissue to be treated. The tissue may be free to move in the treatment container, or may be restrained from gross movements. The flow may be part of a circulation system having a reservoir, with a heater being provided to heat the treatment solution in the reservoir. Alternatively, a treatment apparatus, including a fluid circulation system if desired, may be enclosed in an incubator. The tissue may be mounted in a planar configuration generally parallel to the direction of fluid flow. A flow column having a plurality of sections divided by perforated baffles may be used to treat multiple tissues at once.

37 Claims, 9 Drawing Sheets

U.S. PATENT DOCUMENTS

| | | | |
|---|---|---|---|
| 4,405,327 | 9/1983 | Pollock | 8/94.11 |
| 4,624,822 | 11/1986 | Arru et al. | 264/544 |
| 4,648,881 | 3/1987 | Carpentier et al. | 623/11 |
| 4,770,665 | 9/1988 | Nashef | 8/94.11 |
| 4,786,287 | 11/1988 | Nashef et al. | 8/94.21 |
| 4,800,603 | 1/1989 | Jaffe | 8/94.11 |
| 4,911,713 | 3/1990 | Sauvage | 623/1 |
| 4,990,131 | 2/1991 | Dardik et al. | 600/36 |
| 5,002,566 | 3/1991 | Carpentier et al. | 623/2 |
| 5,068,086 | 11/1991 | Sklenak et al. | 422/21 |
| 5,104,405 | 4/1992 | Nimni | 623/2 |
| 5,116,564 | 5/1992 | Jansen et al. | 264/255 |
| 5,131,908 | 7/1992 | Dardik et al. | 600/36 |
| 5,275,954 | 1/1994 | Wolfinbarger | 436/74 |
| 5,279,612 | 1/1994 | Eberhardt | 8/94.11 |
| 5,447,536 | 9/1995 | Girardot et al. | 8/94.11 |
| 5,595,571 | 1/1997 | Jaffe et al. | 8/94.11 |
| 5,632,778 | 5/1997 | Goldstein | 623/11 |
| 5,773,285 * | 6/1998 | Park | 435/286.5 |
| 5,792,603 * | 8/1998 | Dunkelman et al. | 435/1.2 |
| 5,882,918 * | 3/1999 | Goffe | 435/286.6 |

* cited by examiner

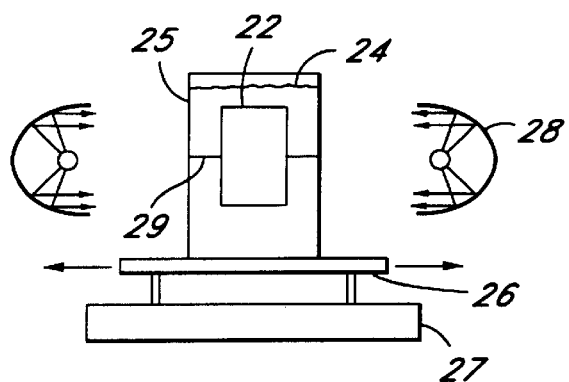
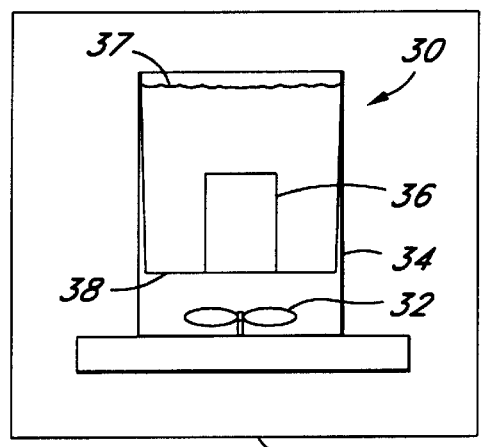
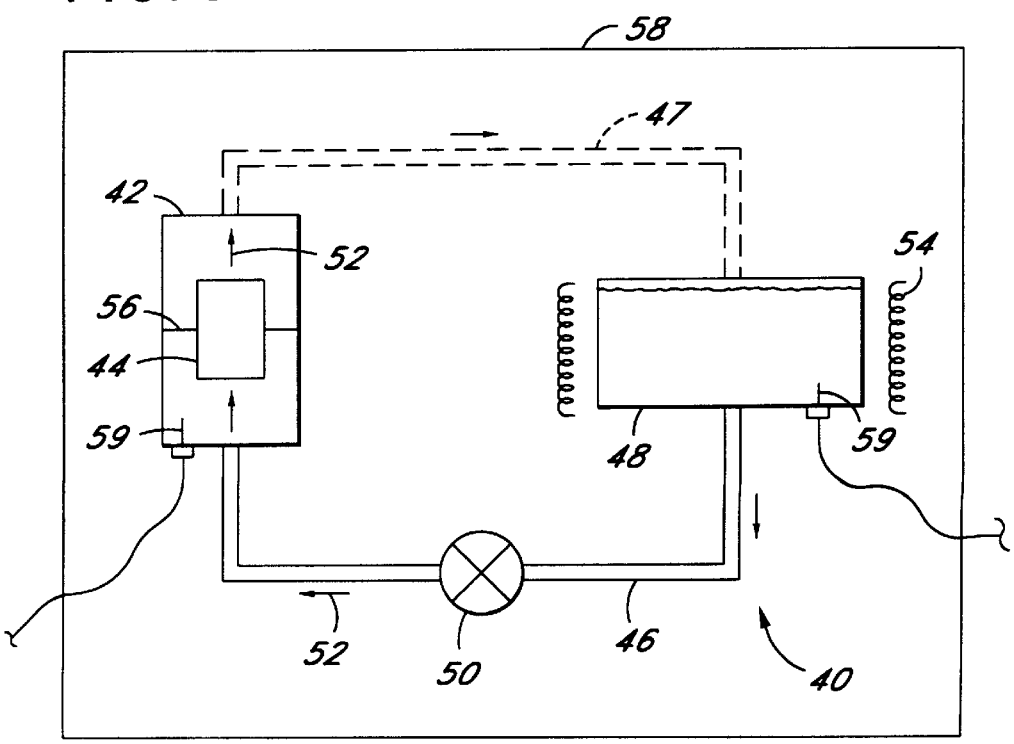

APPARATUSES FOR TREATING BIOLOGICAL TISSUE TO MITIGATE CALCIFICATION

RELATED APPLICATIONS

The present application is a divisional of U.S. application Ser. No. 08/874,180, filed Jun. 13, 1997, now U.S. Pat. No. 5,931,969 entitled "Methods and Apparatuses for Treating Biological Tissue to Mitigate Calcification", which is a continuation of U.S. application Ser. No. 08/282,358, filed on Jul. 29, 1994, now abandoned.

FIELD OF THE INVENTION

The present invention pertains generally to apparatuses for preparing biomedical materials, and more particularly to an apparatus for preparing preserved biological tissue, such as bovine pericardium, for implantation in a mammalian body that induces relative treatment fluid/tissue motion.

BACKGROUND OF THE INVENTION

The prior art has included numerous methods for preserving or fixing biological tissues, to enable such tissues to be subsequently implanted into mammalian bodies. Examples of the types of biological tissues that have heretofore been utilized for surgical implantation include cardiac valves, vascular tissue, skin, dura mater, pericardium, ligaments and tendons.

The term "grafting" as used herein is defined as the implanting or transplanting of any living tissue or organ (See Dorlands Illustrated Medical Dictionary, 27th Edition, W. B. Saunders Co. 1988). Biological tissues which are grafted into the body of a mammal may be xenogeneic (i.e., a xenograft) or allogeneic (i.e., an allograft). The term "bioprosthesis" defines many types of biological tissues chemically pretreated before implantation (Carpentier—See Ionescu (editor), Biological Tissue in Heart Valve Replacement, Butterworths, 1972). As opposed to a graft, the fate of a bioprosthesis is based upon the stability of the chemically treated biological material and not upon cell viability or host cell ingrowth. Chemical pretreatment includes the "fixing" or tamning of the biological tissue. Such fixing or tanning of the tissue is accomplished by exposing the tissue to one or more chemical compounds capable of cross-linking collagen molecules within the tissue.

Various chemical compounds have been utilized to fix or cross-link biological tissues including formaldehyde, glutaraldehyde, dialdehyde starch, hexamethylene diisocyanate and certain polyepoxy compounds.

In particular, glutaraldehyde has proven to be relatively physiologically inert and suitable for fixing various biological tissues for subsequent surgical implantation (Carpentier, A., J. Thorac. Cardiovasc. Surg. 58:467–68 (1969)). In particular, examples of the types of biological tissues which have heretofore been subjected to glutaraldehyde fixation include porcine bioprosthetic heart valves and bovine pericardial tissues.

Clinical experience has revealed that glutaraldehyde-fixed bioprosthetic tissues may tend to become calcified. Such calcification of glutaraldehyde-fixed bioprosthetic tissues has been reported to occur most predominantly in pediatric patients see, Carpentier et al. and "Continuing Improvements in Valvular Bioprostheses, J. Thorac Cardiovasc. Surg. 83:27–42, 1982. Such calcification is undesirable in that it may result in deterioration of the mechanical properties of the tissue and/or tissue failure. In view of this, surgeons have opted to implant mechanical cardiovascular valves into pediatric patients, rather than to utilize glutaraldehyde-preserved porcine valves. However, pediatric patients who receive mechanical valve implants require long term treatment with anticoagulant medications and such anticoagulation is associated with increased risk of hemorrhage.

The mechanism by which calcification occurs in glutaraldehyde-fixed bioprosthetic tissue has not been fully elucidated. However, factors which have been thought to influence the rate of calcification include:

a) patient's age
b) existing metabolic disorders (i.e., hypercalcemia, diabetes, kidney failure . . . )
c) dietary factors
d) race
e) infection
f) parenteral calcium administration
g) dehydration
h) distortion/mechanical factors
i) inadequate coagulation therapy during initial period following surgical implantation; and
j) host tissue chemistry Methods for treating fixed biological tissue so as to inhibit calcification thereof following implantation in a mammalian body tend to substantially increase the usable life of such tissue subsequent to implantation in a mammalian body, thereby mitigating the requirement for subsequent tissue replacement. As those skilled in the art will appreciate, such tissue replacement frequently causes substantial trauma to the patient, occasionally resulting in the patient's death. As such, it is greatly beneficial to be able to either avoid or postpone the need for the replacement of implanted biological tissue.

Various efforts have been undertaken to find ways of mitigating calcification of glutaraldehyde fixed bioprosthetic tissue. Included among these calcification mitigation techniques are the methods described in U.S. Pat. No. 4,885,005 (Nashef et al.) SURFACTANT TREATMENT OF IMPLANTABLE BIOLOGICAL TISSUE TO INHIBIT CALCIFICATION; U.S. Pat. No. 4,648,881 (Carpentier et al.) IMPLANTABLE BIOLOGICAL TISSUE AND PROCESS FOR PREPARATION THEREOF; U.S. Pat. No. 4,976,733 (Girardot) PREVENTION OF PROSTHESIS CALCIFICATION; U.S. Pat. No. 4,120,649 (Schechter) TRANSPLANTS; U.S. Pat. No. 5,002,2566 (Carpentier) CALCIFICATION MITIGATION OF BIOPROSTHETIC IMPLANTS; EP 103947A2 (Pollock et al.) METHOD FOR INHIBITING MINERALIZATION OF NATURAL TISSUE DURING IMPLANTATION; WO84/01879 (Nashef et al.) SURFACTANT TREATMENT OF IMPLANTABLE BIOLOGICAL TISSUE TO INHIBIT CALCIFICATION; U.S. Pat. No. 5,595,571 (Jaffe) BIOLOGICAL MATERIAL PRE-FIXATION TREATMENT; and WO95/11047 (Levy et. al.) METHOD OF MAKING CALCIFICATION-RESISTANT BIOPROSTHETIC TISSUE.

Although some researchers believe that glutaraldehyde actually increases the risk of calcification, it is still the most accepted fixation solution. For example, the Levy patent application noted above utilizes an alcohol treatment for mitigating calcification, in addition to a glutaraldehyde fixation There is significant research occurring into the extent the mechanisms mentioned above cause calcification. Many processes are believed to mitigate calcification, without their proponents knowing exactly why. Indeed, the Levy patent does not offer a mechanism why alcohol is effective in calcification mitigation, other than it is preferred over aldehydes.

A number of tests are conventionally used to gauge the efficacy of various calcification mitigation treatments. The most reliable test is actual implantation into a living organism, preferably a human. Of course, such host studies are by their nature long-term and the results somewhat skewed by the variations present in each individual host. Researchers are therefore constrained to predict the ultimate calcification mitigation benefits of a particular treatment by using laboratory tests on treated tissue, such as calcium uptake studies. Ultimately, there is a substantial amount of extrapolation from the empirical data of such laboratory tests, and to date there is no one predominant mechanism recognized for mitigating calcification.

There remains a need for the development of new methods for inhibiting or mitigating calcification of chemically fixed biological tissue.

SUMMARY OF THE INVENTION

These, as well as other advantages of the present invention will be more apparent from the following description and drawings. It is understood that changes in the specific structure shown and the described may be made within the scope of the claims without departing from the spirit of the invention.

The present invention provides a method for treating at least partially fixed biological tissue to inhibit calcification of the tissue following implantation in a mammalian body, comprising immersing the tissue in a treatment solution, inducing relative and repeated tissue/solution movement, and beating the solution during the step of inducing. The step of inducing may comprise flowing treatment fluid across the tissue and restraining the immersed tissue from gross movement, or enclosing the treatment solution in a container and either shaking the container or stirring the solution within the container, with the immersed tissue floating free or being restrained from gross movement within the container. The step of heating may be applying beat to the outside of the container to indirectly heat the solution therein, or placing the treatment container in an enclosure and heating the enclosure. Alternatively, the step of heating may comprise applying heat directly to the treatment solution.

The present invention also includes a method for treating at least partially fixed biological tissue to inhibit calcification of the tissue following implantation in a mammalian body, comprising positioning the tissue in a flow container; restraining the tissue from gross movement within the container, flowing treatment solution through the flow container into contact with the tissue, and heating the solution during the step of flowing. The step of restraining may comprise mounting the tissue in a planar configuration substantially parallel to the direction of flow of the flowing solution. The tissue may be positioned within a flow container having a cross-section oriented substantially normal to the direction of flow of the flowing solution, the tissue being positioned downstream of a baffle to create a substantially uniform downstream flow profile over the cross-section. In one embodiment, treatment solution is supplied to an inlet of the flow container from a reservoir, and fluid is expelled from an outlet of the flow container to the reservoir. The treatment solution may be heated in the reservoir. Preferably, the treatment fluid flows upward through the flow container from the inlet to the outlet and into contact with the tissue.

In accordance with the invention, an apparatus for treating at least partially fixed biological tissue to inhibit calcification of the tissue following implantation in a mammalian body is provided. The apparatus comprises a flow container, a supply of treatment fluid, a fluid input to the container, a fluid output from the container, a tissue mount for positioning the at least partially fixed biological tissue within the container between the input and output and restrain its gross movement therein, and means for heating the fluid. The flow container is preferably divided into at least two sections in series separated by perforated baffles, with at least one tissue mount in each section. The flow container may be an elongated tube and the baffles circular. The tissue mount may be configured to mount the tissue in a planar configuration substantially parallel to the direction of flow of the solution flowing through the container. The apparatus may additionally include at least one baffle positioned in the flow container and upstream of the tissue mount, the baffle being configured to create a substantially uniform downstream flow profile over a cross-section of the flow container.

BRIEF DESCRIPTION OF THE DRAWINGS

FIG. 3 is a schematic view of an exemplary tissue treatment apparatus including a closed treatment container and container movement device;

FIG. 4 is a schematic view of another exemplary tissue treatment apparatus including an open treatment container and fluid stirring rod;

FIG. 6 is a schematic view of an exemplary tissue treatment apparatus including a treatment container positioned in a flow stream;

DESCRIPTION OF THE PREFERRED EMBODIMENTS

The detailed description set forth below in connection with the appended drawings is intended as a description of the presently preferred embodiment of the invention, and is not intended to represent the only form in which the present invention may be constructed or utilized. The description sets forth the functions and sequence of steps for constructing and operating the invention in connection with the illustrated embodiment. It is to be understood, however, that the same or equivalent functions and sequences may be accomplished by different embodiments that are also intended to be encompassed within the spirit and scope of the invention.

Figure 1:
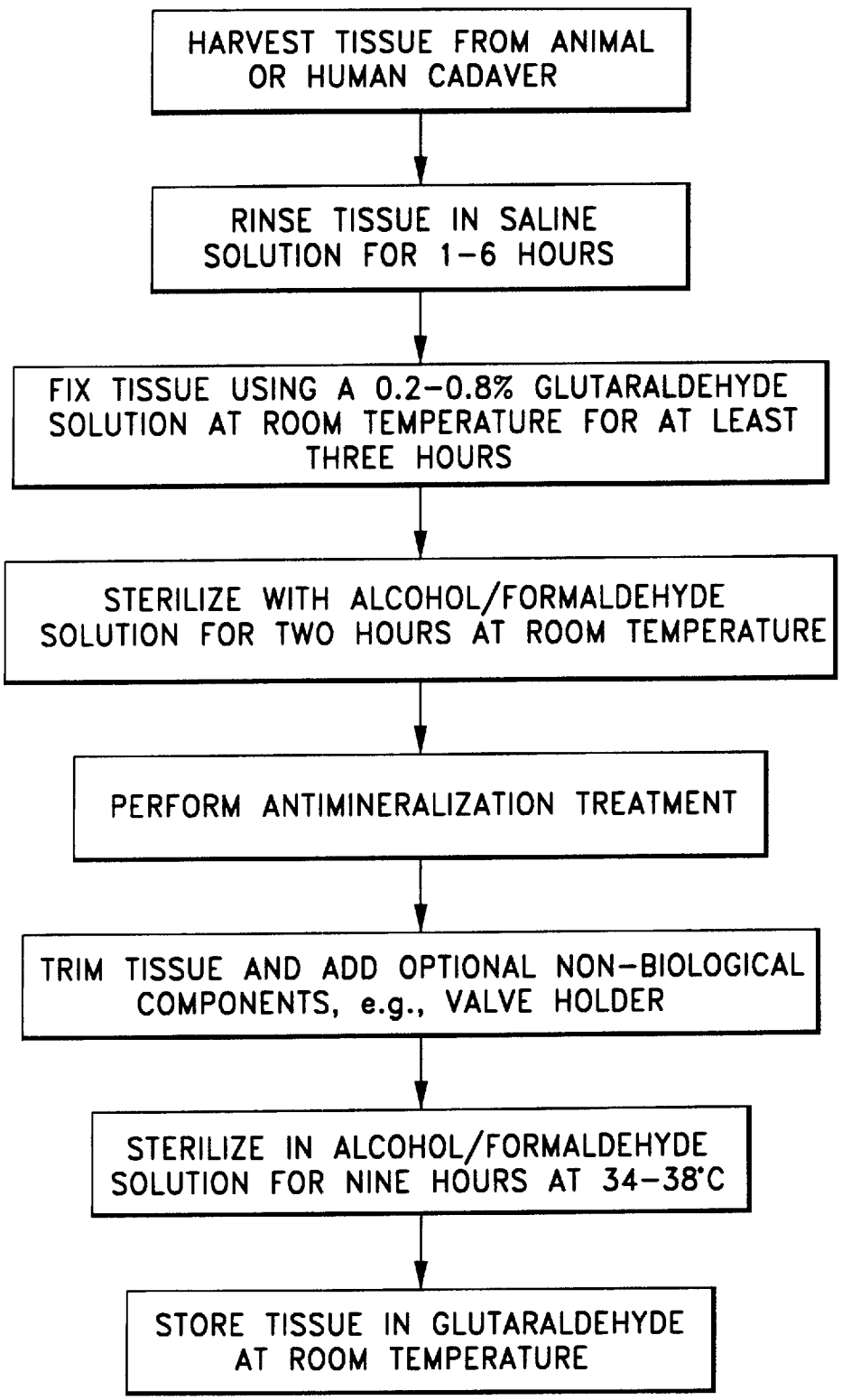
FIG. 1 is a flow diagram illustrating the prior art process for preparing biological tissue for implantation within a mammalian body comprising fixing of the biological tissue with a glutaraldehyde solution.
Figure 2:
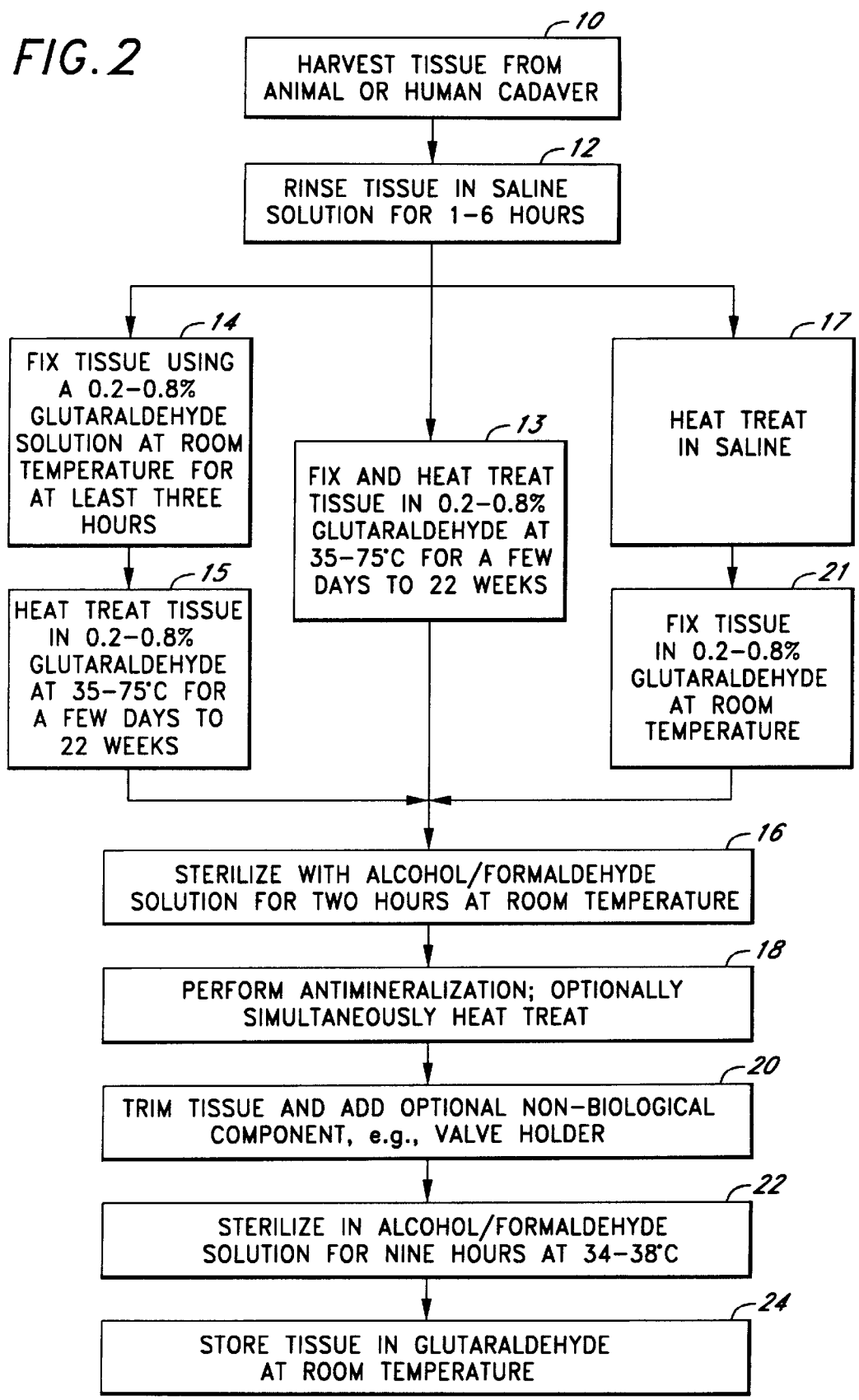
FIG. 2 is a flow chart of the preparation of biological tissue for implantation in a mammalian body comprising a method for inhibiting calcification of the biological tissue according to the present invention.

One method for treating glutaraldehyde fixed biological tissue to inhibit calcification thereof following implantation in a mammalian body is illustrated in FIG. 2 which depicts a flow chart of the presently preferred embodiment of the invention. FIG. 1 depicts a flow chart of the prior art method for preparing biological tissue for implantation within a mammalian body.

Referring now to FIG. 1, the prior art process for preparing biological tissue for implantation within a mammalian body comprises first harvesting the tissue from an animal or human cadaver 10. As those skilled in the art will recognize, various different types of tissue are routinely harvested from different animals and/or human cadavers. For example, heart valves are routinely harvested from pigs, pericardium is routinely harvested from cows or pigs, and skin is routinely harvested from human cadavers. Those skilled in the art will further recognize that new tissues are, from time to time, being found to be implantable within a mammalian body.

After harvesting, the biological tissue is rinsed in saline solution, typically for a period of 1–6 hours 12.

The tissue is next fixed using a buffered glutaraldehyde solution of adequate concentration, for example between 0.2% and 0.8%, at room temperature for at least 3 hours 14. As is well known, glutaraldehyde effects cross-linking of the proteins, e.g., collagen, within the tissue. Such cross-linking tends to make the tissue more durable and effects preservation thereof. It is known that cross-linked protein exhibits increased resistance to proteolytic cleavage and further that one of the major processes by which circulating blood may destroy tissue is via enzymatic activity which involves unfolding of the protein substrate in order to facilitate enzymatic hydrolysis. Cross-linking of the protein of a tissue makes the tissue resistant to such unfolding, and consequently tends to prevent deterioration thereof due to the enzymatic activity of blood.

The tissue is next sterilized, preferably with an alcohol/formaldehyde solution for 2 hours at room temperature 16. The preferred solution for effecting sterilization of the tissue comprises approximately 12 ml/l of Tween 80; approximately 2.65 gms/l of $MgCl_2 \cdot H_2O$; approximately 108 ml/l of formaldehyde (37%); approximately 220 ml/l of ethyl alcohol (100%) and approximately 4.863 gms/l of HEPES buffer. The balance of the solution comprises double filtered $H_2O$. The pH of the solution is typically adjusted to 7.4 via the addition of NaOH. Those skilled in the art will recognize various other sterilization solutions are likewise suitable.

Antimineralization treatment 18 is optionally performed so as to inhibit the accumulation of mineral deposits upon the biological tissue after implantation of a mammalian body. As those skilled in the art will recognize, various different antimineralization treatments are utilized so as to prevent the deposition of various different minerals upon the biological tissue.

The tissue is trimmed and any non-biological components are then added thereto 20. For example, it is common to sew a heart valve to a valve holder which aids in the handling thereof and which may additionally function as a mount for the valve when implanted into a mammalian body.

Next, the biological tissue is once again sterilized 22, preferably in an alcohol/formaldehyde solution as discussed above. Since preparation of the biological tissue is substantially complete and the biological tissue will next likely be stored for an extended period of time, a more rigorous sterilization procedure from that previously utilized is typically employed. At this stage, the biological tissue is typically sterilized for approximately 9 hours at 34–38° C.

After sterilization, the biological tissue is stored in glutaraldehyde at room temperature 24.

Tissue Treatment Using Heat

Referring now to FIG. 2, a method for treating glutaraldehyde fixed biological tissue to inhibit calcification thereof following implantation in a mammalian body comprises the additional step of heating preferably when the glutaraldehyde is in contact with the biological tissue, to approximately 35–75° C. for approximately 4–22 weeks, and more preferably for a period of a few days to 22 weeks.

The treatment fluid should be heated to a temperature greater than body temperature (37° C.) but not high enough to damage either the tissue or the treatment fluid. Thus, the preferred heat range is between 35–75° C. However, the temperature affects the amount of calcification mitigation, and the process time, and is preferably between 45° C. and 55° C., and more preferably between 50° C.±1° C.

Heating of the biological tissue may be performed at any time after harvesting the tissue from the animal or human cadaver and prior to implanting the tissue within a mammalian body. However, heating of the biological tissue is preferably performed at a point in the process for preparing the biological tissue when the biological tissue is already disposed within a bath of glutaraldehyde solution, as occurs at various stages of the process according to the prior art. Thus, the method for treating glutaraldehyde fixed biological tissues according to the present invention is preferably performed either during fixing thereof with a glutaraldehyde solution, immediately after fixing thereof with the glutaraldehyde solution, or alternatively just prior to or after being stored in a glutaraldehyde solution.

As a further alternative, a method for treating glutaraldehyde fixed biological tissues may be performed during antimineralization treatment by adding glutaraldehyde to the antimineralization solution and heating the solution, preferably to approximately 35–75° C. for approximately 4–22 weeks. More preferably, the tissue is heat treated at 50° C.±1° C. for a period of a few days to 22 weeks.

For example, after fixing tissue using a buffered glutaraldehyde solution of adequate concentration, for example between 0.2% and 0.8%, at room temperature for at least 3 hours 14, the biological tissue may be heat treated in either the same or different glutaraldehyde solution, preferably at approximately 35–75° C. for a few days to 22 weeks 15.

As one of the alternatives discussed above, the biological tissue is fixed and heat-treated simultaneously 13 in the 0.2–0.8% glutaraldehyde solution, again preferably at approximately 35–75° C. for approximately a few days to 22 weeks. Another alternative is to heat the tissue in saline 17 prior to fixation 21.

As the other alternative discussed above, the biological tissue may simultaneously undergo antimineralization treatment and heat treatment 19. Glutaraldehyde is added to the antimineralization solution so as to effect the inhibition of calcification of the tissue following implantation in a mammalian body.

Tissue Treatment Using Relative Tissue/Fluid Movement

FIG. 3 illustrates one preferred embodiment of a tissue treatment system 20 of the present invention. One or more pieces of tissue 22 or leaflets are immersed in a treatment solution 24 within a closed container 25. The container 25 rests on a shaker table 26 which reciprocates relative to a base 27 in one or more directions. One particularly preferred type of shaking device is an orbital shaker. In one exemplary embodiment, the orbital shaker 26 is actuated at a rotational speed of approximately 55 RPM. The container 25 and contents therein may be subjected to heating, such as with radiant heaters 28 as illustrated. Of course, any number of means for heating the container 25 are known, such as resistance heaters, convective flow, and the like.

The solution 24 is preferably a buffered glutaraldehyde, but may be any chemical solution, such as Denacol® or others, which performs substantially the same in this context. The shaking and/or heat may be applied during fixation or after. The tissue is preferably at least partially fixed prior to being subjected to the calcification mitigation treatment described herein, and more preferably the tissue is fully fixed prior to the treatment. The treatment thus can be designed to complete the fixation process. In a preferred embodiment, tissue that has been fixed for a period of between thirty minutes to fourteen days is placed in the container 25 with a buffered clutaraldehyde solution of adequate concentration, for example between 0.2% and 0.8%. The solution is then shaken for thirty minutes after which the container 25 remains static for fourteen days.

The tissue 22 may be sheets of bovine pericardium tissue, precut leaflets, or fully formed porcine heart valves. One potential disadvantage of using precut leaflets or porcine heart valves is the tissue's nonuniform capacity for shrinkage during calcification mitigation treatment. It can be difficult, though not impossible, to consistently and accurately compensate for this phenomenon. A detailed map of the fiber orientation, thickness and other properties of each individual leaflet may be required to predict the final form of the leaflet after treatment. Therefore, the preferred procedure is to place sheets or pieces of tissue in the container and subject it to the shaking and/or heat. Afterwards, the leaflets are cut from the treated tissue.

It will be noted that the tissue 22 within the solution 24 may be allowed to move about freely. In another embodiment, and as will be described below with respect to the embodiment of FIG. 6, the tissue may be restrained from gross movement but allowed to freely shrink, such as with a device schematically shown at 29.

In another variation on the shaking, a treatment system 30 is shown in FIG. 4 wherein a stirring rod 32 is positioned in a container 34 to replace the shaking table 28. The stirring rod is preferably actuated magnetically through the container, but may also comprise a shaft driven apparatus. The stirring rod 32 is preferably designed so as not to batter the tissue 36 but instead just to cause gentle movement of the fluid 37 relative to the tissue. Therefore, in the illustrated embodiment, a piece of filter paper 38, or other such similar porous substrate or mesh, is draped over the top rim of the container and the tissue pieces 36 placed therein. In this way, the stirring rod 32 imparts rotational or other momentum to the fluid 37 in the container 34, but the tissue 36 remains above the damaging action of the rotating rod. Also shown in FIG. 4 is a heated enclosure or incubator 39 within which is placed the entire apparatus 30.

In another version of shaking, multiple flasks or containers holding the treatment fluid and tissue samples are clamped to a rotating ferris-wheel apparatus. The apparatus includes a wheel rotating about a tilted axis so that the flasks follow a tilted circular trajectory. In this manner, the fluid within the flasks gently washes over the tissue pieces as the wheel rotates.

The containers 25 and 34 in FIGS. 3 and 4 may be open or closed, primarily depending on the nature of the treatment fluid. Glutaraldehyde is a toxic substance which evaporates to create a dangerous gas. Thus, treatment with glutaraldehyde is preferably done in a closed container. On the other hand, some substances like Denacol® may be less hazardous and the container may be left open under a hood, for example.

Relative movement between the tissue and the treatment fluid is believed to enhance calcification mitigation. A mechanism for this result has not been fully formulated, although mass transport of the fluid surrounding the tissue may be relevant. Indeed, one theory is that certain cell material, for example, proteins, is extracted or removed from the tissue by the treatment fluid, which removal is enhanced relative to static treatment methods by the movement of the fluid. In other words, the relative movement of the tissue within the fluid repeatedly replenishes the fluid surrounding any one portion of tissue. Test results shown in FIGS. 12 and 13 for samples of tissue treated in a variety of ways in accordance with the present invention indicate that the combination of heat and relative tissue/fluid movement decreases the amount of calcium uptake after implantation in rats, suggesting that such treatment will mitigate calcification in long or short term implantation in humans.

Figure 5:
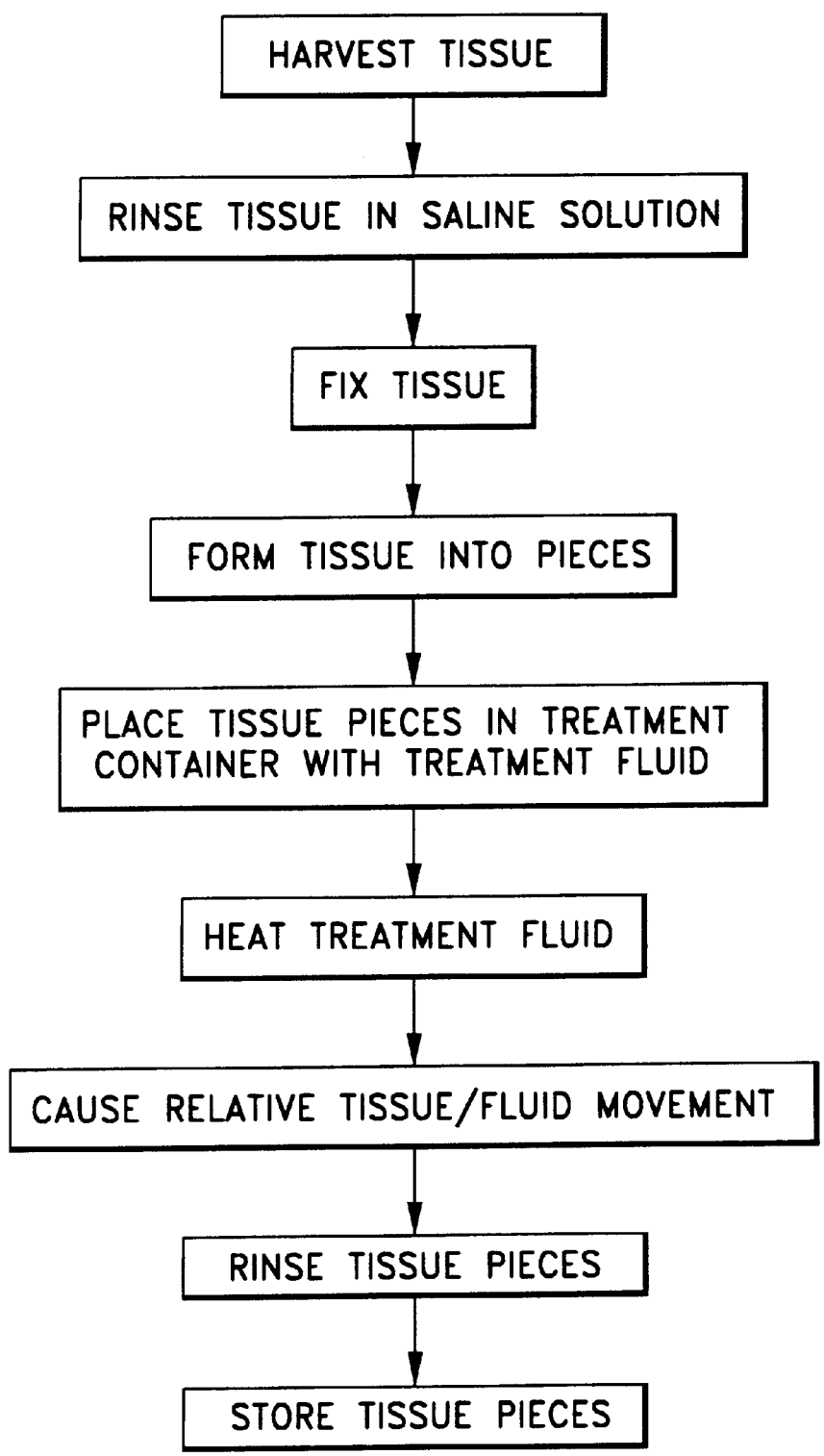
FIG. 5 is a flow chart of the preparation of biological tissue using the system of FIG. 3 or 4 including the application of heat and motion to a treatment solution.

FIG. 5 is a flowchart showing a preferred method for treating tissue using the system shown in FIGS. 3 or 4. Many of the specific pre- and post-treatment steps described with respect to FIGS. 1 and 2 have been left out for clarity, but remain applicable. Initially, the tissue is harvested, rinsed, fixed and cut into pieces, preferably squares or rectangles, from which leaflets may be formed. The pieces of tissue are then immersed in the treatment fluid within the container, and the fluid heated to a predetermined temperature. Relative movement between the tissue pieces and surrounding treatment medium is induced and continued for a predetermined time. Inducing relative tissue/fluid movement may be accomplished by any of the configurations shown herein, such as shaking or vibrating a container for the tissue and fluid, or by flowing treatment fluid onto the tissue. Finally, the tissue pieces are removed from the container, rinsed and stored for later use. Of course, rather than storing the tissue, it may be formed directly into leaflets and assembled into a heart valve directly after the treatment process.

The solution is heated indirectly through the surrounding air, such as with the radiant heaters 28 shown in FIG. 3, to a temperature of about 50° C. plus or minus 1° C. The container is shaken or the fluid is stirred to cause relative tissue/fluid movement. The treatment time ranges between fourteen days to two months, but is preferably closer to two months. The container 25 is preferably a glass tissue culture flask having a volume of approximately 250 ml., and the solution is a buffered glutaraldehyde solution of adequate concentration, for example between 0.2% and 0.8%. As mentioned above, a number of pieces of tissue 22 may be treated at a single time within the container 25. One proposed ratio of tissue to solution is approximately 12 leaflets or leaflet-sized pieces of tissue per every 150 ml of solution.

Tissue Treatment Using Relative Tissue/Fluid Flow

FIG. 6 illustrates schematically another variation on a treatment system 40 which utilizes flow past the tissue as opposed to shaking a container or stirring the fluid in which the tissue is placed. A flow creates the relative motion between the treatment solution and the tissue which is believed to result in the beneficial calcification mitigation effects.

The system 40 comprises a flow container 42 within which tissue 44 is placed. A number of conduits 46 connect one end of the flow container 42 to a pump 50 and then to a solution reservoir 48. Conduit 47, shown in dashed line, may be coimected between the other end of the flow container 42 and the reservoir 48 to complete a closed circulation loop. The pump propels treatment solution through the system 40 in the direction shown by the arrows 52. The tissue 44 is preferably restrained within the flow container 42 using means schematically illustrated at 56. Resistance heaters 54 are illustrated surrounding the reservoir 48. If immersion heaters are used, they must be able to withstand the extended exposure to sometimes caustic treatment fluid. Of course, one or both of the resistance heating elements 54 may be removed from around the reservoir, or alternative heating devices may be used. For example, treatment system 40, and the system 20 or 30 shown in FIGS. 3 and 4, for that matter, may be enclosed in a larger enclosure or room 58 which is heated to the preferred temperature by internal or external heaters. In the illustrated embodiment, thermocouples 59 are provided to sense the temperature within both the flow container 42 and the reservoir 48. The thermocouple 59 in the reservoir is preferably connected to feedback electronics for controlling the heaters 56 based on the temperature of the fluid in the reservoir. This is so that the temperature does not rise too high to a level which might be detrimental to the tissue. The temperature within the flow container is monitored using a thermocouple both as a safety, and to record the precise temperature profile of the treatment fluid.

Figure 7:
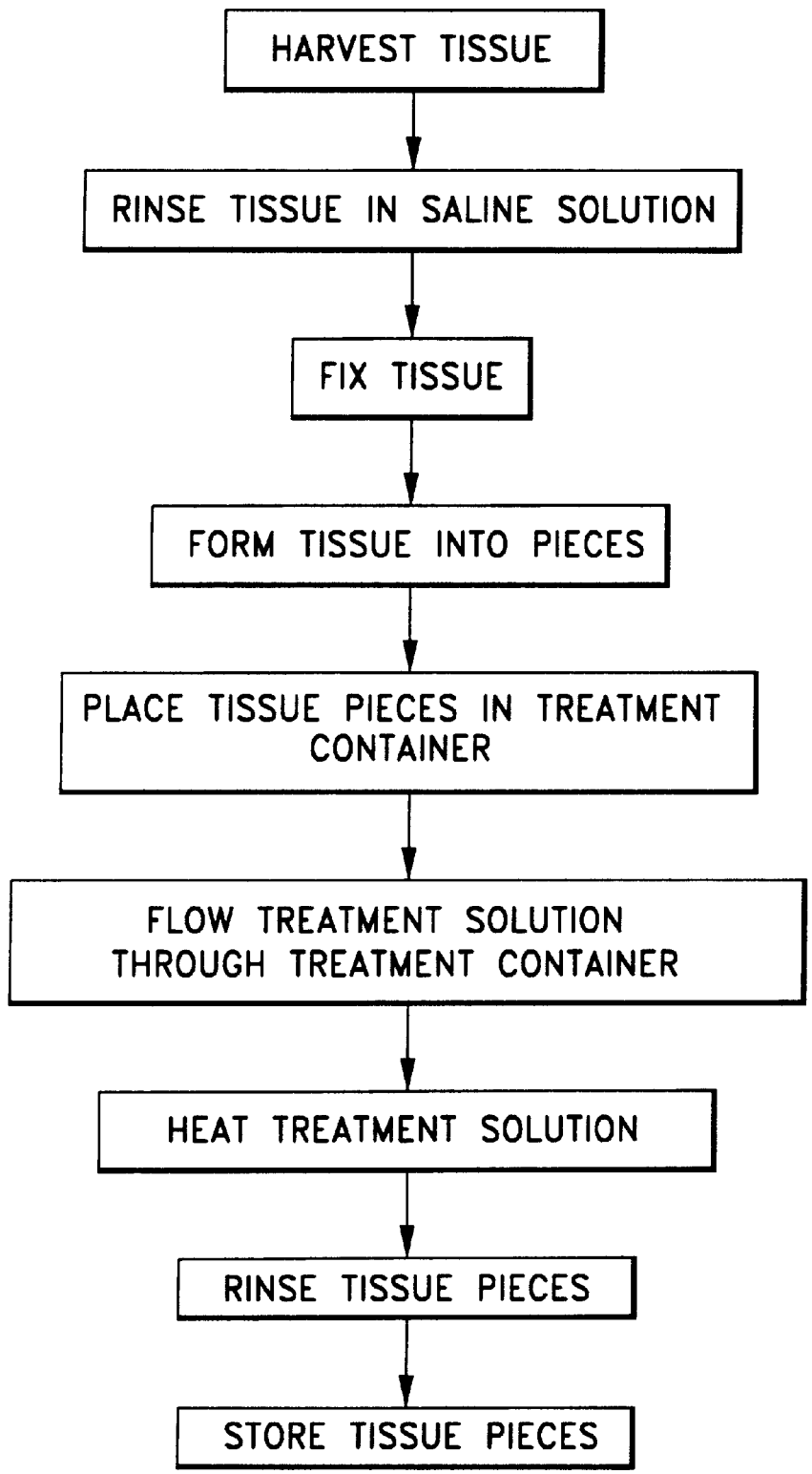
FIG. 7 is a flowchart of the preparation of biological tissue using the system of FIG. 5 including the application of heat and flow of treatment solution past the tissue.

The basic elements of a method for treating tissue using the system 40 are illustrated in FIG. 7. Initially, the tissue is harvested, rinsed, fixed and cut into pieces, preferably squares or rectangles, from which leaflets may be formed. The tissue (or leaflets in some instances) may be placed within the flow container 42 and subjected to flow during or after fixation. In a preferred embodiment, the tissue 44 is at least partially fixed before being subjected to the flow within the system 40, and more preferably the tissue is fully fixed prior to the treatment. The pieces of tissue are then placed in the treatment container, and the solution caused to flow therethrough, initiating relative movement between the tissue pieces and surrounding treatment medium which is continued for a predetermined time. The solution is heated directly outside of the container, or indirectly by heating the container. Finally, the tissue pieces are removed from the container, rinsed and stored for later use. Of course, rather than storing the tissue, it may be formed directly into leaflets and assembled into a heart valve directly after the treatment process.

With reference to FIG. 6, the tissue is first fixed for a period of between thirty minutes to fourteen days and placed in the flow container 42. In an alternative, the tissue may be first placed within the container 25 shown in FIG. 3 and shaken for a period of thirty minutes. After the fixation (or after the shaking, if desired), the tissue is placed in the flow container 42 and subjected to solution flow of between ten and fifteen gallons per minute (38–57 lpm) for a period of between fifteen to sixty days. The solution is preferably heated directly within the reservoir 48 to a temperature of about 50° C. (122° F.). The solution is preferably a 0.2–0.8% buffered glutaraldehyde, and the tissue 44 is restrained from movement but allowed to shrink.

In an alternative method of treating tissue in the system 40, the treatment time is between thirty and sixty days. The flow rate is approximately 7.4 gallons per minute (28 lpm) on average, and is uniform throughout a cross section normal to the flow within the flow container 42. The tissue 44 is preferably a rectangle of bovine pericardium of about 2 inches by 4 inches in dimension. This size of tissue sample may be used to form one or two leaflets after treatment.

Those with skill in the art will recognize that variations to the above mentioned systems and processes for moving the fluid and/or heating the tissue are available. For example, the flow of solution past the tissue may be combined with a vibrational or shaking motion of the flow container 42 to enhance any calcification mitigation benefits derived from either method. Additionally, though the system 40 is shown as a closed circulation device, fresh solution may be pumped to the flow container 42 and discharged after passing through the container (thus the conduit 47 is shown as optional). Of course, this will require a significant amount of treatment solution which may be prohibitively expensive. Nevertheless, one of the theoretical mechanisms for the beneficial aspects of the present treatment method including flow is that the solution is constantly replenished in the region surrounding the tissue so that a maximum mass transport of chemicals and/or biological material such as protein is realized from the tissue to the solution. Thus, a system which inputs fresh treatment solution, rather than recycling it through a reservoir, would theoretically be more effective in this regard.

Flow Column Apparatus

Figure 8:
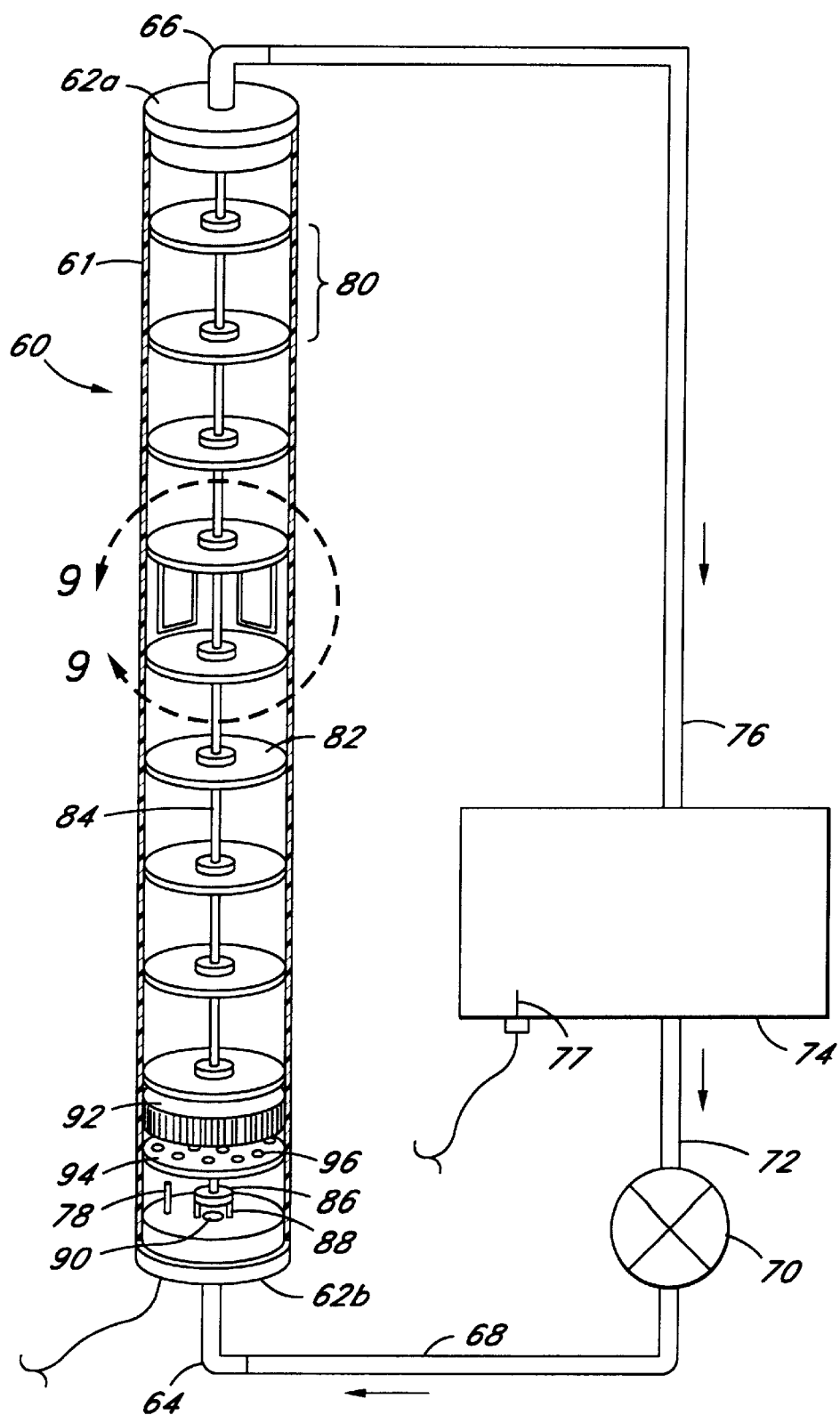
FIG. 8 is a perspective view of another preferred tissue treatment apparatus including an upstanding flow column and a plurality of vertical sections within which tissues to be treated are mounted.

FIG. 8 illustrates a perspective view of a flow column 60 which may represent the flow container 42 illustrated schematically in FIG. 6. The column 60 is preferably a clear acrylic tube 61 having an inner diameter of approximately six inches (15.2 cm), a height of about six feet (1.8 m), and a capacity of about ten gallons (38 l). The top and bottom ends of the cylinder 60 are closed by caps 62a and 62b, respectively, which are sealed against the inner surface of the cylinder 60 with O-rings (not shown). A lower inlet fitting 64 centered in the cap 62b provides a conduit for introducing treatment fluid to the lower end of the cylinder 60. Likewise, an upper fitting 66 connected to the cap 62a provides an outlet for the treatment fluid. A length of hose 68 connects the lower fitting 64 to a fluid pump 70, which is in turn connected by a hose 72 to a fluid reservoir 74. A length of hose 76 connecting the upper fitting 66 to the reservoir 74 completes the circulatory treatment system. Those with skill in the art will understand the fluid connections and requirements, which will not be described further herein.

As mentioned above, the solution within the reservoir 74 is preferably directly heated to the desired treatment temperature. Although not illustrated, the reservoir is desirably provided with one or more immersion resistance heaters. A thermocouple 77 senses the temperature of the reservoir and is preferably connected to feedback electronics for controlling the immersion heater so that the solution temperature does not rise too high to a level which might be detrimental to the tissue. The temperature within the flow container is monitored using a thermocouple 78 both as a safety, and to record the precise temperature profile of the treatment fluid. Excessive temperatures can detrimentally affect the treatment solution itself, and thus the heating must be done gradually and with a heater having good temperature control.

The vertical flow column or cylinder 60 is segmented into a plurality of vertical sections 80 (seen enlarged in FIG. 9) by a number of regularly spaced baffles 82 having perforations 83. The baffles are substantially circular perforated disks positioned horizontally within the vertical cylinder 60, normal to the fluid flow. The outer diameter of each baffle 82 contacts, or comes into close proximity with, the inner surface of the tube 61. Although the flow column 60 is illustrated vertically, other arrangements will work. However, the vertical flow orientation is preferred to help purge bubbles from the flow column at start up. In other words, the bubbles naturally migrate out of the flow column in a very short time, as opposed to a horizontal flow path, for example. It should be also be noted that the perforations are not shown in FIGS. 8 and 9 for clarity, but are shown in FIG. 10.

The baffles 82 are commonly mounted on a vertical support rod 84 extending along the axis of the cylinder 60. The support rod 84 contacts the lower ceiling cap 62b and extends upward into close proximity to the upper cap 62a. As seen at the lower end of FIG. 8, the support rod 84 preferably terminates in a stand member 86 having a pair of bifurcated legs 88 which contact the top surface of lower cap 62b on either side of an inlet aperture 90. In this manner, the support rod 84 can be positioned along the axis of the cylinder 60 while not occluding inlet flow from the pump 70.

As mentioned above, the baffles 82 divide the cylinder 60 into a plurality of vertical sections 80. In this respect, the vertical sections 80 include the region between two baffles 82. In the illustrated embodiment, there are eight such vertical sections 80 having a height of between seven and eight inches (17.8–20.3 cm). The entire height of the column 60 is approximately 6 feet (1.8 m), and thus there is some space left above the top baffle and below the bottom baffle. The baffles 82 are slidably mounted on the support rod 84 to enable adjustment of the spacing therebetween, if desired. Furthermore, the tissue pieces 82 can be easily mounted when the baffles 82 are removed from the system, whereupon the baffles are slid over the support rod which is then positioned within the tube 61. The tissue pieces to be treated are mounted in a particular manner in a circumferential array about the support rod 84, as will be apparent from the description of FIGS. 9–11.

At the top of the cylinder 60 a vertical space is created between the upper baffle and the upper cap 62a, in which the central support rod 84 terminates. The space is needed to insure that the flow passing through upper baffle 82 is not unduly disturbed so that the flow within the upper vertical section 80 remains uniform in a horizontal cross section. Indeed, the uniformity of flow across any horizontal cross section between the baffles is important in the present configuration to insure that the flow past any one piece of tissue is equal to the flow past other tissues. The primary mechanism for insuring such uniform flow is the baffles 82 themselves. Preferably, the perforations 83 are sufficiently numerous and have a sufficient diameter so that the cross-sectional area of the baffles 82 has less structural material than open flow channels. The baffles 82 are thus designed to maintain a uniform, non-laminar upward flow stream through each flow section 80.

At the lower end of the cylinder 60, below the lowest baffle 82, a flow straightener 92 is positioned just above a velocity reducer plate 94. Inlet flow through the aperture 90 thus passes upward through the velocity reducer plate 94 and flow straightener 92 to impinge on the lowest baffle 82. The velocity reducer plate 94 is a disc like plate having a plurality of apertures 96 formed therein. The apertures are relatively widely spaced in the plate 94 to create a drag on the flow and slow its velocity. The flow straightener 92 resembles a honeycomb structure with a relatively densely spaced number of individual flow channels, and has a vertical dimension greater than the velocity reducer plate 94 or baffles 82. Flow enters the column 60 through the aperture 90 and continues upward through the velocity reducer plate 94 and straightener 92. After flow passes through the straightener 92, it impinges on the lowest baffle 82. The treatment solution flows upward through each baffle 82 into each successive section 80 and out the top of the column 60. The column 60 is initially filled with air which is forced out as the surface of the upwardly advancing treatment solution flow passes upward through the column.

Figure 9:
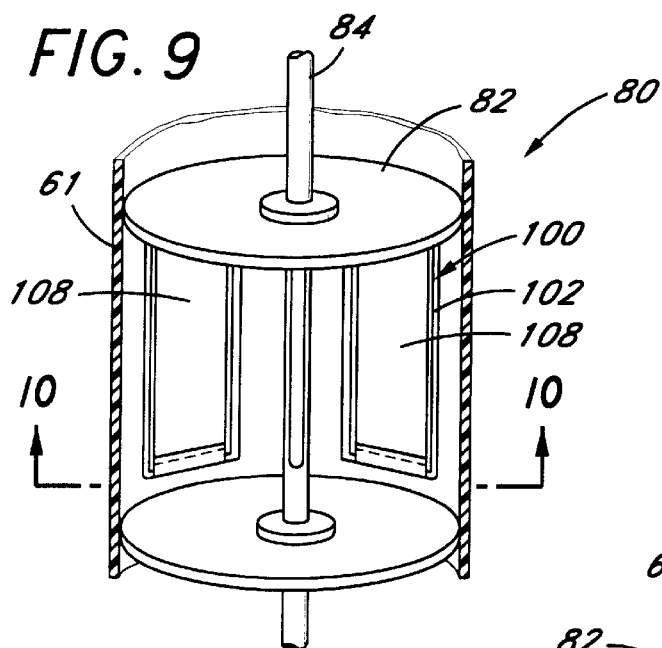
FIG. 9 is an enlarged perspective view of one vertical segment of the flow column of FIG. 8 illustrating a piece of tissue suspended from a baffle in a flow stream.
Figure 10:
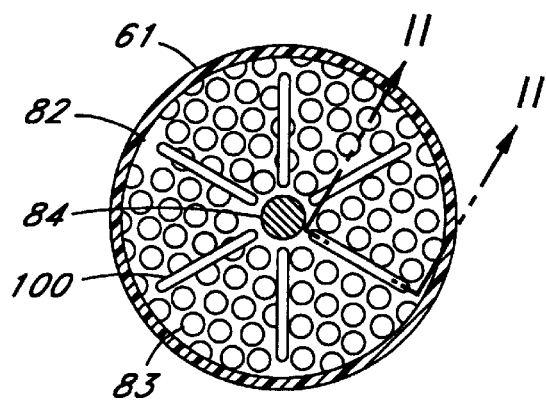
FIG. 10 is a horizontal cross section taken along line 10—10 of FIG. 9 through one vertical section of the flow column.
Figure 11:
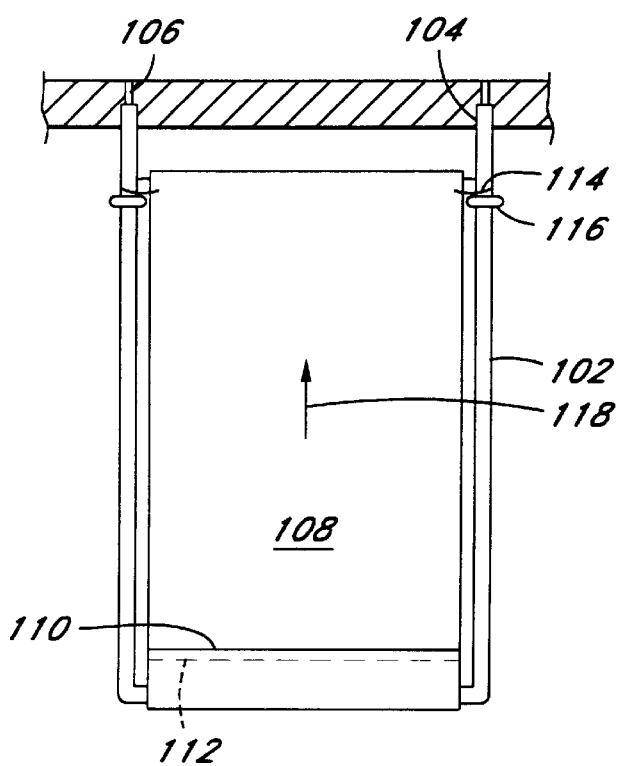
FIG. 11 is a vertical cross section taken along line 11—11 of FIG. 10 and through a baffle and tissue suspension mount.

Now with reference to FIG. 9, a vertical section 80 is enlarged illustrating a plurality of tissue mounts 100 depending from the upper baffle 82. The tissue mounts 100 comprise U-shaped members 102, more clearly shown in FIG. 11. FIG. 10 shows the circumferential array of mounts 100 surrounding the central support rod 84. Each mount 100 has a generally rectangular configuration and is oriented radially in the baffle 82. That is, free ends of the U-shaped members 102 insert within similarly sized downwardly opening apertures 104 in the baffle 82. One of the apertures 104 for each mount 100 is positioned close to the support rod 84, while the other is positioned close to the tube 61. The apertures 104 extend approximately halfway through the thickness of the baffle 82 and a smaller diameter through hole 106 continues upward to the top surface of the baffle. This hole 106 is needed to push the mounts 100 from the apertures 104 when treatment is finished. Preferably, the legs of the U-shaped members 102 are spread outward a slight amount so that they have to be squeezed together to fit into the two apertures 104. This ensures a tight fit so the mounts 100 will not fall out of the apertures 104.

Rectangular tissue pieces 108 are attached to the mounts with sutures or other similar expedient. In the illustrated embodiment, a lower edge 110 of each tissue piece 108 loops around the bridge portion of the U-shaped member 102 and is sewn to the main body of the tissue piece along line 112. In this way, the leading edge of the tissue piece 108 in the upward flow stream is rounded, and thus protected from friction induced tearing or wear. One or more sutures 114 connect the upper corners of the tissue piece 108 to the upper ends of the legs of the U-shaped members 112. Preferably the tissue piece 108 is only connected at one or two locations along its vertical length to prevent gross movement or flapping of the tissue, while allowing the maximum freedom for the tissue to shrink. An O-ring 116 or other such device placed on each leg of the member 112 prevents the sutures 114 from sliding down the leg. The upward flow 118 of treatment solution also assists in maintaining the generally planar configuration of each tissue piece 108.

Mounting the tissue pieces 108 in a planar configuration substantially parallel to the direction of flow of the solution ensures that an even amount of solution contacts both sides of the tissue. That is, is the tissue pieces were canted with respect to the flow, the backsides would be exposed to less direct flow, and eddy currents and the like might be set up, further making the fluid exposure nonuniform. In addition, the preferred parallel orientation minimizes any stretching of the tissue during the extensive treatment period, such as might occur if the fluid was directed to one face of the tissue or the other.

The radial orientation of the plane of each tissue piece 108 desirably ensures uniform contact with treatment solution during flow through the column 60. Ideally, the baffles 82 include perforations 120, seen in FIG. 10, which create the uniform, nonlinear flow. The same velocity of solution is produced at any radial point from the support rod 84 outward. Of course, different pieces of tissue 108 have been shown to possess widely different properties, even from the same pericardial sac. Nevertheless, the present treatment configuration is designed to maximize the uniformity of conditions seen by each piece of tissue 108. There may be some variation in treatment conditions between the top and bottom reaches of the container due to fluid head differences, but applicants believe that such variations are minimal for the six foot tall column 60 described herein.

There are preferably eight vertical sections 80 in which six tissue pieces 108 are mounted for a total of forty-eight tissue pieces being treated at once. Of course, other numbers of sections and tissue pieces per section are possible. The present flow column is extremely well-suited for consistently manufacturing high quality treated bioprosthetic tissue. The segmented flow column with uniform flow, and vertical orientation of each tissue piece 108 provides high uniformity of treatment. The modular nature of the column with the entire support rod 84 having all of the baffles 82 attached thereto is a significant advantage in manufacturing. One batch of tissues may be treated, and then removed so that after flushing the system a new batch can be ready for installation and treatment. Furthermore, the flow column lends itself to a high degree of control over the system parameters such as the relative tissue/fluid velocity and the temperature. Significantly, there are no large stagnant zones of flow within the column, and especially not within each vertical segment 80.

Rat Subcutaneous Studies

Figure 12:
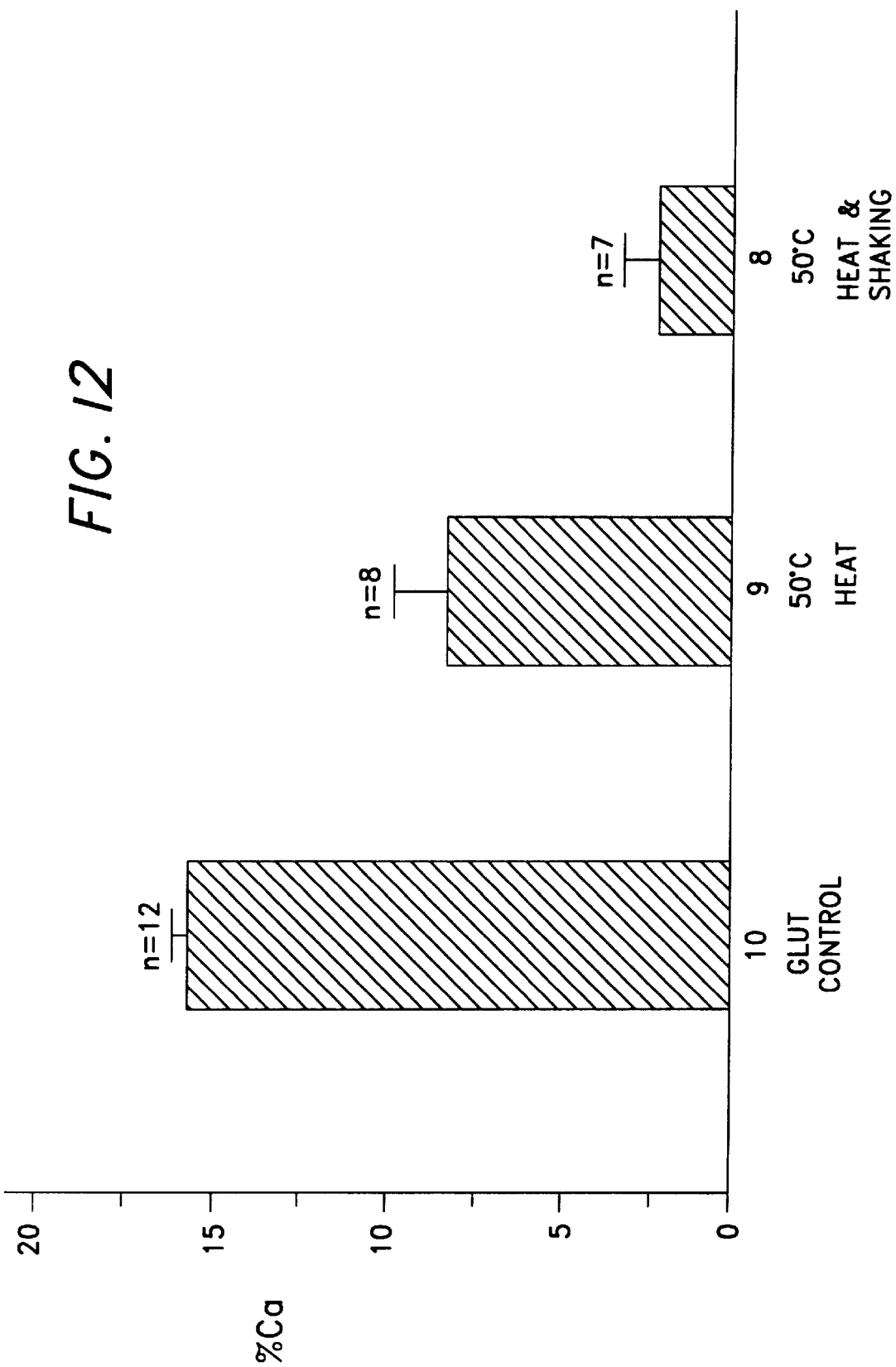
FIG. 12 is a bar graph comparing the measured calcium uptake in bovine pericardium tissues treated in a conventional manner, solely with heat, and with heat and motion.
Figure 13:
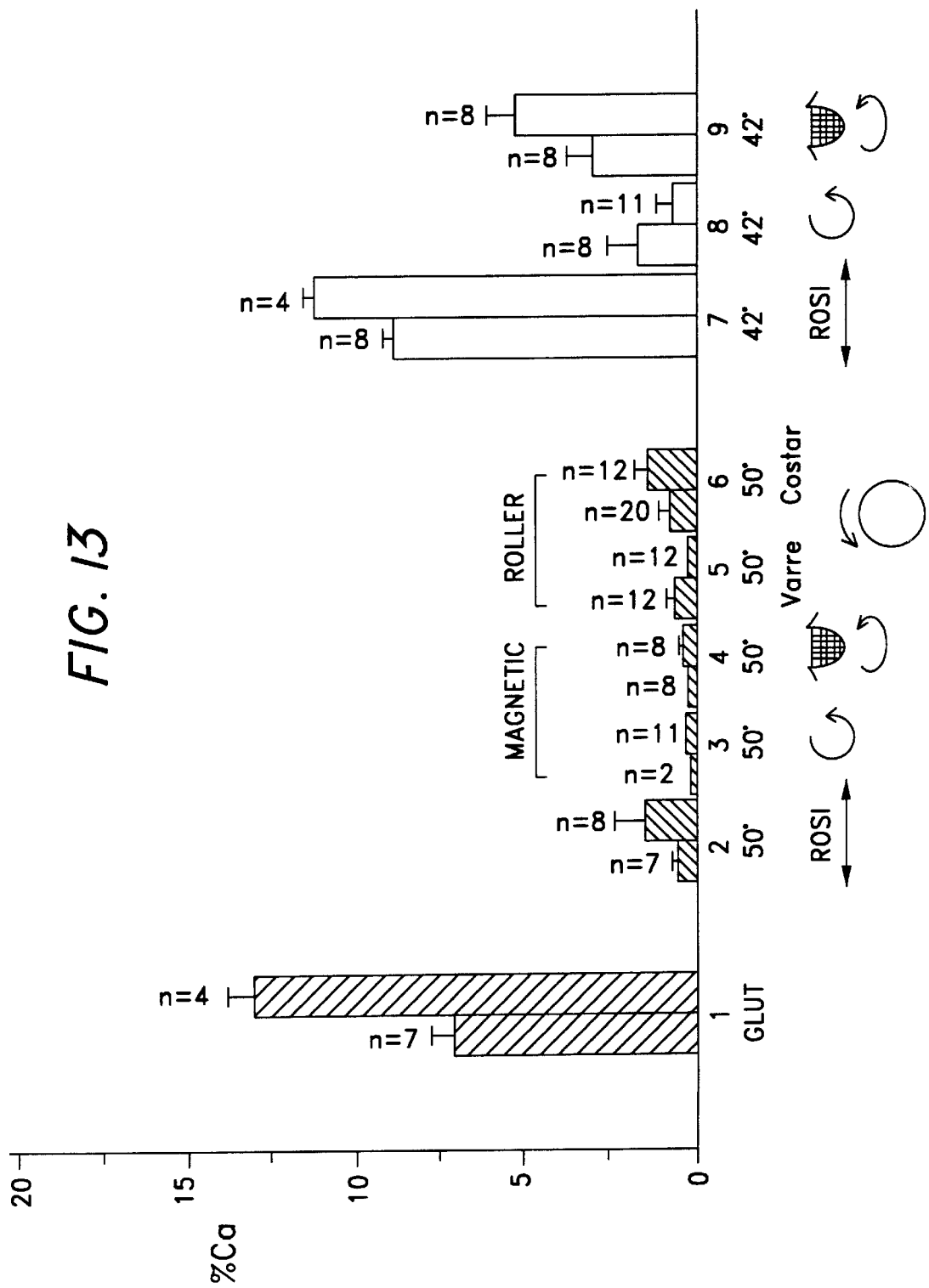
FIG. 13 is a bar graph comparing the measured calcium uptake in bovine pericardium tissues treated in a conventional manner and with heat and motion from various sources.

FIGS. 12 and 13 are results of calcium uptake measurements from tissue treated in a variety of ways, implanted subcutaneously in rats for several months, and then removed. These graphs indicate that heat alone reduces calcium uptake in comparison with a control, and that heat and motion reduces the calcium uptake even further. A number of shaking, stirring or movement apparatuses were used at two different temperatures, with the same general results.

FIG. 12 shows the results from three groups of samples of untreated and treated bovine pericardium tissue. The first group (GLUT CONTROL) exhibited an average measurement of about 16% calcium from 12 tissue samples which were subjected to a post-fixation treatment of unheated and static glutaraldehyde. The second group (HEAT) exhibited an average measurement of about 7% calcium from 8 tissue samples which were subjected to a post-fixation treatment of static glutaraldehyde heated to a temperature of 50° C. Finally, the third group (HEAT AND SHAKING) exhibited an average measurement of about 4% calcium from 7 tissue samples which were subjected to a post-fixation treatment of static glutaraldehyde heated to a temperature of 50° C. The treatment solution for all three groups was identical—0.6% HEPES-glutaraldehyde at a pH of 7.4—and the treatment period was equal—2 months. The third group was shaken in a bottle or container using a reciprocal orbital shaker actuated at 80 RPM. The rats were all approximately 12 days old, and the tissue samples were left implanted for eight weeks.

FIG. 13 shows the results from a number of groups of samples of untreated and treated bovine pericardium tissue. The calcium uptake results for the groups are indicated by bars with different shading depending on the overall treatment regimen. Thus, the black bars for group 1 are the control (no heat or shaking), the middle shaded bars are for samples subjected to shaking and heat treated to 50° C., and the right-hand white bars are for samples subjected to shaking and heat treated to 42° C.

Group 1 on the left is a control and shows results for two subgroups of 7 and 4 samples each. The control samples were treated for 2 months in 0.6% HEPES-glutaraldehyde at a pH of 7.4 with no heat or movement. Each sample was implanted in 16 day old rats, and left implanted for a period of between 3 and 4 months before being removed to test for calcium.

Groups 4–6 in the middle were all heat treated at 50° C. in the same treatment solution as group 1 for the same period. The differences between the treatment regimen for groups 2–6 are the methods used to induce relative tissue/fluid movement. The methods are shown graphically below each group. Group 2–7 includes two subgroups of 7 and 8 samples each subjected to reciprocal orbital shaking. Group 3–7 includes two subgroups of 2 and 11 samples each placed in a flask with a magnetic stirring bar in the bottom. Group 4 is the same method as group 3 but with two subgroups of 8 samples each placed on a filter instead of being allowed to float around the flask. Group 5 included two subgroups of 12 samples each placed in a first container and subjected to a rolling motion, using a tilted ferris wheel arrangement. Group 6 included two subgroups of 20 and 12 samples each placed in a second container and also subjected to a rolling motion.

Groups 7–9 on the right were all heat treated at 42° C. in the same treatment solution as groups 1–8 and for the same period. Again, the differences between the treatment regimen for groups 7–9 are the methods used to induce relative tissue/fluid movement, shown graphically below each group. Group 7 includes two subgroups of 8 and 4 samples each subjected to reciprocal orbital shaking. Group 8 includes two subgroups of 8 and 11 samples each placed in a flask with a magnetic stirring bar in the bottom. Group 9 is the same method as group 8 but with two subgroups of 8 samples each placed on a filter instead of being allowed to float around the flask.

It is apparent from these tests that the shaking and heat treatment reduced calcium intake over the control group, as well as over the heat treatment alone. Also, treatment at 50° C. was substantially more effective than treatment at 42° C. Comparisons of the different shaking/stirring methods indicates that stirring with a magnetic rod within the flask produced the least amount of calcium uptake, regardless of temperature, although perhaps not by a significant margin at 50° C.

It is understood that the exemplary methods and apparatuses for treating glutaraldehyde fixed biological tissue described herein and shown in the drawings represent only presently preferred embodiments of the present invention. Indeed, various modifications and additions may be made to such embodiments without departing from the spirit and scope of the invention. For example, various fixing agents, such as Denacol® or aldehydes other than glutaraldehyde, may exhibit properties similar to those of glutaraldehyde so as to make them suitable for use in the present invention and, thus, may likewise be utilized. Accordingly, these and other modifications and additions may be obvious to those skilled in the art and may be implemented to adapt the present invention for use in a variety of different applications. Furthermore, the scope of the invention should be determined with reference to the appended claims.

What is claimed is:

1. An apparatus for treating at least partially fixed biological tissue to inhibit calcification of the tissue following implantation in a mammalian body, comprising:

a flow container;

a reservoir containing treatment fluid suitable for fixing the tissue;

a fluid input to the container;

a fluid output from the container;

a tissue mount for positioning the at least partially fixed biological tissue within the container between the input and ouput and restrain its gross movement therein; and means for heating the fluid to a temperature greater than body temperature (>37° C.) comprising a heater for heating fluid in the reservoir.

2. The apparatus of claim 1, wherein the flow container is divided into at least two sections in series separated by perforated baffles, with at least one tissue mount in each section.

3. The apparatus of claim 2, wherein the flow container is an elongated tube and the baffles are circular.

4. The apparatus of claim 1, wherein the tissue mount is configured to mount the tissue in a planar configuration substantially parallel to the direction of flow of the solution flowing through the container.

5. The apparatus of claim 1, further including at least one baffle positioned in the flow container and upstream of the tissue mount, the baffle being configured to create a substantially uniform downstream flow profile over a cross-section of the flow container.

6. The apparatus of claim 5, wherein the baffles are perforated plates oriented substantially normal to the direction of flow of the solution flowing through the container, and the flow container is divided into at least two sections in series, each two adjacent sections being separated by a baffle, with at least one tissue mount in each section removably secured to one of the baffles.

7. The apparatus of claim 1, further including a sensor for monitoring the fluid temperature in the reservoir, and a feedback control loop responsive to the sensed temperature for adjusting the heater temperature.

8. The apparatus of claim 1, wherein the flow container comprises an upstanding tube, the fluid input being located at the lower end of the tube and the fluid output being located at the upper end of the tube, the apparatus further comprising a velocity reducer above the fluid input, and a flow straightener above the velocity reducer and below the first tissue mount.

9. An apparatus for treating at least partially fixed biological tissue to inhibit calcification of the tissue following implantation in a mammalian body, comprising a piece of at least partially fixed biological tissue;

a container suitable for containing tissue treatment fluid and immersing the piece of at least partially fixed biological tissue in the fluid;

a shaker for causing treatment fluid movement within the container;

means for heating the treatment fluid and tissue within the container; and means for restraining the immersed tissue from gross movement within the container.

10. The apparatus of claim 9, wherein the piece of at least partially fixed biological tissue is a bioprosthetic heart valve leaflet.

11. The apparatus of claim 9, wherein the shaker is an orbital shaker.

12. An apparatus for treating at least partially faced biological tissue to inhibit calcification of the tissue following implantation in a mammalian body, comprising:

a piece of at least partially fixed biological tissue, a container suitable for containing tissue treatment fluid and immersing the piece of at least partially fixed biological tissue in the fluid, means for causing treatment fluid movement within the container comprising a stirrer immersed in the treatment fluid, means for heating the treatment fluid; and means for restraining the immersed tissue from gross movement within the container.

13. The apparatus of claim 12, wherein the stirrer is a stirring rod.

14. The apparatus of claim 13, further including a shaft drive for the stirring rod.

15. The apparatus of claim 13, further including a magnetic drive for the stirring rod.

16. The apparatus of claim 12, wherein the means for restraining tissue from gross movement within the container comprises a porous substrate separating the tissue from the stirrer.

17. The apparatus of claim 16, wherein the container has an open mouth and the porous substrate is draped over the open mouth and separates the container into an upper portion for receiving the tissue and a lower portion for receiving the stirrer.

18. The apparatus of claim 12, wherein the means for heating comprises a heater adjacent to the container that applies heat to the outside of the container and indirectly heats the treatment fluid therein.

19. The apparatus of claim 18, wherein the heater comprises a resistive heater.

20. The apparatus of claim 12, wherein the means for heating comprises a heater that applies heat directly to the treatment fluid.

21. The apparatus of claim 12, wherein the heater is external to the container.

22. The apparatus of claim 21, wherein the heater comprises a convective flow heater.

23. An apparatus for treating an at least partially fixed sheet of biological tissue to inhibit calcification of the tissue following implantation in a mammalian body, comprising:

treatment fluid suitable for fixing the tissue, a container suitable for containing the tissue treatment fluid having a fluid input and a fluid output;

a system for continuously flowing the treatment fluid through the flow container between the input and output;

a tissue mount for positioning the at least partially fixed sheet of biological tissue within the container between the input and output and restrain its gross movement therein, the tissue mount being adapted to mount the tissue sheet in a planar configuration substantially parallel to the direction of flow of the treatment fluid, the sheet of biological tissue being immmersed in the continuous flow of treatment fluid; and means for heating the treatment fluid.

24. The apparatus of claim 23, wherein the flow container has a cross-section oriented substantially normal to the direction of flow of the treatment fluid, the apparatus further including a baffle positioned upstream of the mount which creates a substantially uniform downstream flow profile over the container cross-section in the region of the mount.

25. The apparatus of claim 24, further comprising a plurality of perforated baffles dividing the flow container into a series of sections, and a plurality of said mounts in each section for mounting multiple tissue pieces within each section.

26. The apparatus of claim 23, further comprising a reservoir external to the container, the flow container having an inlet and an outlet, and a pump for circulating treatment fluid from the reservoir to the flow container and expelling fluid from the flow container outlet back to the reservoir.

27. The apparatus of claim 26, wherein the means for heating heats the treatment solution in the reservoir.

28. An apparatus for treating at least partially fixed biological tissue to inhibit calcification of the tissue following implantation in a mammalian body, comprising:
   a flow container divided into at least two sections in series separated by perforated baffles;
   a supply of treatment fluid;
   a fluid input to the container;
   a fluid output from the container;
   at least one tissue mount in each section for positioning the at least partially fixed biological tissue within the container between the input and output and restrain its gross movement therein; and
   means for heating the fluid.

29. The apparatus of claim 28, wherein the flow container is an elongated tube and the baffles are circular.

30. An apparatus for treating at least partially fixed biological tissue to inhibit calcification of the tissue following implantation in a mammalian body, comprising:
   a flow container;
   a supply of treatment fluid;
   a fluid input to the container;
   a fluid output from the container;
   a tissue mount for positioning the at least partially fixed biological tissue within the container between the input and output and restrain its gross movement therein;
   means for heating the fluid; and
   at least one baffle positioned in the flow container and upstream of the tissue mount, the baffle being configured to create a substantially uniform downstream flow profile over a cross-section of the flow container.

31. The apparatus of claim 30, wherein the baffle is a perforated plate oriented substantially normal to the direction of flow of the solution flowing through the container, and the flow container is divided into at least two sections in series, each two adjacent sections being separated by a baffle, with at least one tissue mount in each section removably secured to one of the baffles.

32. An apparatus for treating at least partially fixed biological tissue to inhibit calcification of the tissue following implantation in a mammalian body, comprising:
   a flow container comprising an upstanding tube;
   a supply of treatment fluid;
   a fluid input to the container at a lower end of the tube;
   a fluid output from the container at an upper end of the tube;
   a tissue mount for positioning the at least partially fixed biological tissue within the container between the input and output and restrain its gross movement therein;
   means for heating the fluid; and
   a velocity reducer above the inlet aperture, and a flow straightener above the velocity reducer and below the first tissue mount.

33. An apparatus for treating at least partially fixed biological tissue to inhibit calcification of the tissue following implantation in a mammalian body, comprising:
   a container suitable for containing tissue treatment fluid;
   means for causing treatment fluid movement within the container including a stirrer immersed in the treatment fluid;
   means for heating the treatment fluid; and
   means for restraining the immersed tissue from gross movement within the container.

34. The apparatus of claim 33, wherein the means for restraining tissue from gross movement within the container comprises a porous substrate separating the tissue from the stirrer.

35. The apparatus of claim 34, wherein the container has an open mouth and the porous substrate is draped over the open mouth and separates the container into an upper portion for receiving the tissue and a lower portion for receiving the stirrer.

36. An apparatus for treating at least partially fixed biological tissue to inhibit calcification of the tissue following implantation in a mammalian body, comprising:
   a flow container suitable for containing tissue treatment fluid;
   a system for flowing treatment fluid through the flow container, wherein the flow container has a cross-section oriented substantially normal to the direction of flow of the treatment fluid;
   means for restraining the tissue from gross movement within the flow container comprising a mount for mounting the tissue in a planar configuration substantially parallel to the direction of flow of the treatment fluid;
   a baffle positioned upstream of the mount which creates a substantially uniform downstream flow profile over the container cross-section in the region of the mount; and
   means for heating fluid.

37. The apparatus of claim 36, further comprising a plurality of perforated baffles dividing the flow container into a series of sections, and a plurality of said mounts in each section for mounting multiple tissue pieces within each section.

* * * * *

UNITED STATES PATENT AND TRADEMARK OFFICE
CERTIFICATE OF CORRECTION

PATENT NO. : 6,210,957 B1
DATED : April 3, 2001
INVENTOR(S) : Sophie Carpentier, Alain F. Carpentier, Lillian J. Quintero, Victor S. Packham, Jong H. Wang, Stefan G. Schreck It is certified that error appears in the above-identified patent and that said Letters Patent is hereby corrected as shown below:

Claim 13,
Line 1, after the word "partially", delete faced
Line 1, after the word "partially", insert fixed.

Signed and Sealed this

Twenty-seventh day of November, 2001

Attest:

NICHOLAS P. GODICI
Attesting Officer    Acting Director of the United States Patent and Trademark Office